United States Patent [19]
Shaw

[11] Patent Number: 5,423,758
[45] Date of Patent: Jun. 13, 1995

[54] RETRACTABLE FLUID COLLECTION DEVICE

[76] Inventor: Thomas J. Shaw, 1510 Hillcrest, Little Elm, Tex. 75068

[21] Appl. No.: 168,659

[22] Filed: Dec. 16, 1993

[51] Int. Cl.⁶ .................. A61M 5/50; A61M 5/32; A61B 5/00
[52] U.S. Cl. ...................... 604/110; 128/763; 604/195
[58] Field of Search .............. 604/192, 195, 196, 110, 604/263; 128/763–766

[56] References Cited

U.S. PATENT DOCUMENTS

| | | | |
|---|---|---|---|
| 2,752,918 | 7/1956 | Uytenbogaart. | |
| 3,046,985 | 7/1962 | Saenz. | |
| 4,813,426 | 3/1989 | Haber et al. | 128/763 |
| 4,838,863 | 6/1989 | Allard et al. | 604/110 |
| 4,838,869 | 6/1989 | Allard | 604/195 |
| 4,841,985 | 6/1989 | Wanamaker | 128/763 |
| 4,850,374 | 7/1989 | Diaz-Ramos | 128/763 |
| 4,871,355 | 10/1989 | Kikkawa | 604/198 |
| 4,904,242 | 2/1990 | Kulli | 604/110 |
| 4,947,863 | 8/1990 | Haber et al. | 128/764 |
| 4,984,580 | 1/1991 | Wanamaker | 128/763 |
| 5,019,044 | 5/1991 | Tsao | 604/110 |
| 5,046,508 | 9/1991 | Weissler | 128/763 |
| 5,067,945 | 11/1991 | Ryan et al. | 604/198 |
| 5,070,885 | 12/1991 | Bonaldo | 128/763 |
| 5,104,378 | 4/1992 | Haber et al. | 604/110 |
| 5,125,414 | 6/1992 | Dysarz | 128/763 |
| 5,180,370 | 1/1993 | Gillespie | 604/110 |
| 5,188,599 | 2/1993 | Botich et al. | 604/110 |
| 5,188,613 | 2/1993 | Shaw | 604/195 |
| 5,193,552 | 3/1993 | Columbus et al. | 128/760 |
| 5,201,710 | 4/1993 | Caselli | 604/110 |
| 5,211,628 | 5/1993 | Marshall | 604/110 |
| 5,336,187 | 8/1994 | Terry et al. | 604/110 |

*Primary Examiner*—John D. Yasko
*Assistant Examiner*—Adam J. Cermak
*Attorney, Agent, or Firm*—Harris, Tucker & Hardin

[57] ABSTRACT

A permanently automatically retractable fluid collecting device has an elongated outer protective tube member having a front end with a port and a coaxial telescoping plunger having a forward end for frictionally engaging a needle holder for a canula needle. The plunger is slidingly mounted in the elongated tube member for selective movement in an axial direction toward and away from the front. The front end of the plunger has an opening having inwardly facing surfaces for frictionally engaging outwardly facing surfaces of the periphery of a needle holder along a slidable axially oriented interface. When the plunger is moved forward to extend the needle from the port, a catch holds it in a first position. Biasing force is applied to the needle holder being frictionally held in the front of the plunger. A sample tube is installable in the opening at the rear of the plunger. After taking a sample and removing the collection tube, a plunger cap is repositioned to allow the plunger to be moved from the first position toward a second position causing sliding separation of the plunger from the needle holder along the slidable interface. The biasing force overcomes remaining frictional holding force at the sliding interface to cause immediate and permanent retraction of the needle holder into a cavity comprising a retraction space within the plunger.

28 Claims, 3 Drawing Sheets

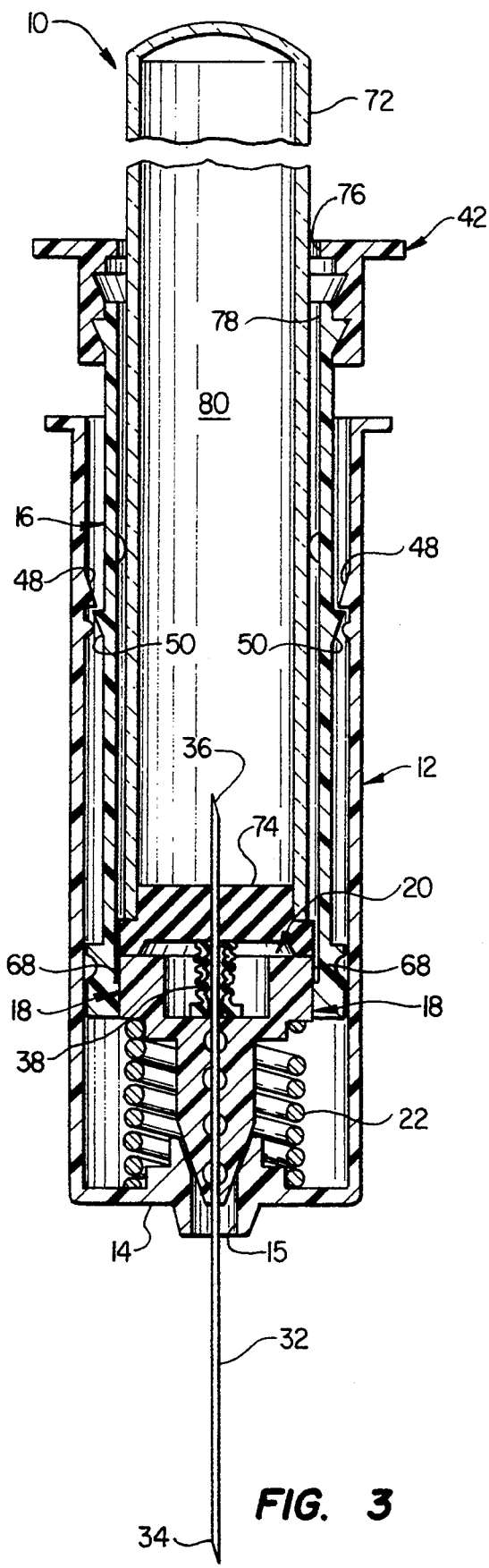
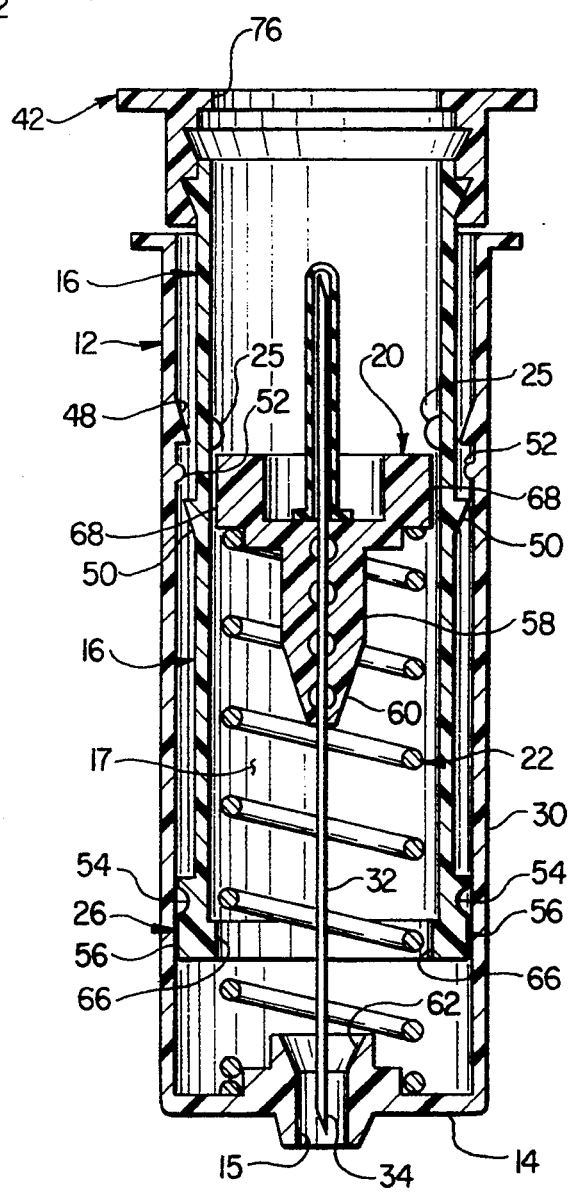
FIG. 3
FIG. 4

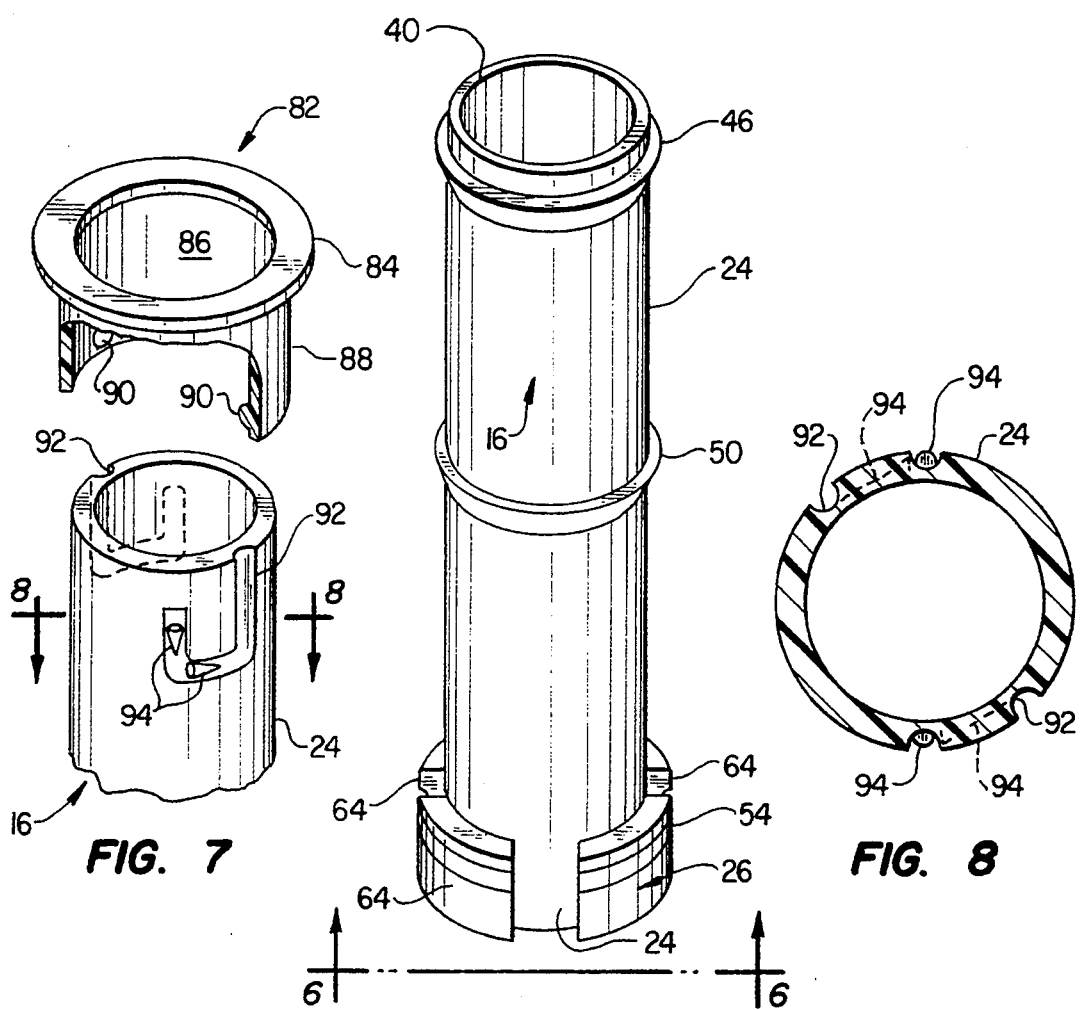
FIG. 7
FIG. 5
FIG. 8
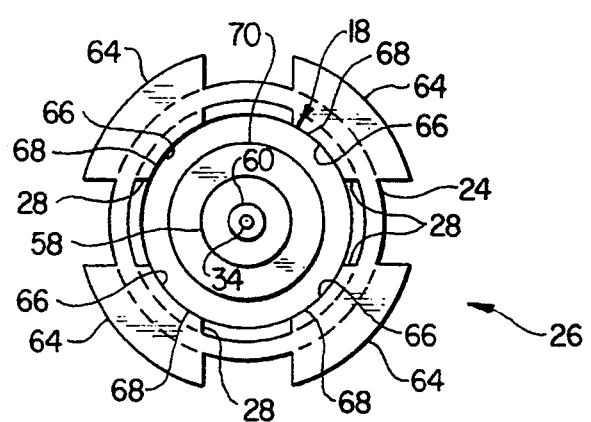
FIG. 6

RETRACTABLE FLUID COLLECTION DEVICE

BACKGROUND OF THE INVENTION

1. Field of the Invention

This invention pertains to a device for collecting body fluid from a subject, and more particularly, to a device which reduces the risk of cross-contamination between the subject and medical personnel.

2. Background of the Prior Art

The recent AIDS epidemic adds a serious and deadly risk factor to taking samples for analysis of a patient's blood. Blood collection devices utilize a needle inserted into a subject's vein so as to draw the blood through the needle into an associated collection reservoir. Accidental needle sticks from previously used needles can occur during the fluid withdrawing process, and subsequent handling and disposal operations.

The most commonly used blood sampling device is sold under the trademark Vacutainer® by Becton Dickinson Corporation. The conventional device of this type has a tubular syringe-like body with a needle in the end, part of which extends back into the tubular syringe-like shell, and part of which extends externally for puncturing the skin. An evacuated collection tube with a rubber stopper is placed into the open back end of the syringe-like shell with the rubber stopper against the internal end of the needle. After the skin is punctured, the collection tube is pushed to cause the needle to enter the evacuated tube, which helps draw blood into the collecting tube. When a sufficient sample has been obtained, the collecting tube and its stopper are simply withdrawn from the tubular shell and sent to the laboratory. The needle is permanently extended from the end of the syringe-like shell into which the collecting tube is placed. Consequently, great care is required in handling a used device.

Some devices used for sampling body fluids employ a needle assembly which is threadably engaged with a needle-holding syringe-like tube. The needle end for insertion into front needle end for puncturing the vein of the patient and a rear needle end for insertion into an evacuated collection tube. After use, the needle assembly is manually handled. It must be unscrewed for disposal or sterilization. Other devices of this type employ a front mounted needle assembly held by an externally positioned latch mechanism which enables the provider to release the needle assembly frontwardly for disposal. The contaminated needle continues to present a danger to those handling the disposal of waste materials. The needle assembly may be forwardly biased with a spring. An example of this type is found in Wanamaker U.S. Pat. No. 4,841,985.

Still other devices provide for retraction of the needle into a shielded safety syringe. There is a cylindrical outer protective sheath and an inner needle carrier movable axially through the sleeve. The needle carrier has a rearwardly biased needle mounted in an inner slidable sleeve within the outer sheath. A position control body connected to the needle carrier extends through a slot in the outer sleeve and is manually movable to allow the needle to be retracted. However, the needle can be re-extended. The retraction is not permanent. Such a device is illustrated by Haber U.S. Pat. No. 4,813,426. Such devices require complicated parts and are expensive to manufacture and assemble.

It would be desirable to have a retractable fluid collection device having few easily assembled economically mass-produced parts which is automatically and permanently retractable. It would be desirable to have such a device which provides a shifting position in which the needle is enclosed without the need for a separate needle guard and easily extended for use without a need to handle or assemble the needle to another part. It would be desirable to have such a device in which consistent reproducible retraction is assured so that the contaminated needle is fully contained within a protective sheath and one in which the retractive mechanism does not depend upon flexing or breaking of pans.

The invention disclosed herein provides the aforesaid features. Other objects and advantages of the invention will become apparent from the following description taken in connection with the accompanying drawings in which an embodiment of this invention is set forth by illustration and example.

SUMMARY OF THE INVENTION

The present invention provides a retractable precisely and easily assembled fluid collection device for use in collecting fluid from a subject. Coaxial telescoping members control the movement of a cannula needle which has fluidly communicating opposite sharpened points, one of which can be extended for venipuncture, while the other is exposed within the telescoping members for insertion through the diaphragm of a removable collection tube. The needle is fixed to a body which is coupled to one of the telescoping members at a slidable interface which frictionally engages the body and allows the needle to be moved to a use position with the needle extended. Safe and sure retraction occurs by restraining the needle-holding body while moving the member which is frictionally engaged with the body to slidingly separate the needle-holding body in the direction of movement along the sliding interface.

The device has an elongated tube member having a front end and a coaxial movable member having a retraction space within. The movable member is slidably mounted within the tube member for axial movement toward and away from the front end of the tube member. A canula needle is held by the retraction body. The retraction body is frictionally held by the movable member along a generally axially oriented slidable interface formed by cooperating generally parallel surfaces of the retraction body and the movable member. A portion of the retraction body which is in frictional engagement with the movable member along the sliding interface is preferably in the form of a ring. The front of the movable member is preferably a head portion having an opening with inwardly facing surfaces which correspond with and engage corresponding outwardly facing surfaces of the preferably ring-shaped portion of the retraction body.

The movable member, together with the frictionally held retraction body, is axially movable in response to selective movement of the movable member toward the front end of the tube member to a first position, and to a second position closer to the front end of the tube member than is the first position. The first position is a use position wherein a needle mounted in the retraction body is extended through a port or opening in the front end of the tube member.

A retraction force is applied to the retraction body by a biasing means tending to cause retraction by driving the retraction body into the retraction space. The biasing member is preferably a spring mounted between the front end of the elongated tube and the retraction body. The spring is compressed as the movable member slides forward to the first position. There is provided a means preventing the retraction body from axial movement in a forward direction beyond the first position. Retraction occurs by sliding release of the retraction body relative to the movable member along the slidable interface, in response to the retraction force when the movable member is moved axially relative to the elongated tube from the first position to the second position. As the slidable interface area is reduced, the frictional holding force is reduced to less than the retraction force of the spring. There is a sudden and permanent separation and retraction of the retraction body into the retraction space a distance sufficient to withdraw a needle into the device.

The movable member may have an axially forwardly positioned head portion having an opening therein with one or more inwardly facing lands comprising the cooperating generally parallel surface of the movable member which frictionally engage the cooperating generally parallel surface of the retraction body to form the slidable interface. The cooperating generally parallel surface of the retraction body comprise an outwardly facing peripheral surface of a portion of the retraction body. The lands may be angularly spaced arcuate segments which engage a circularly-shaped outer peripheral surface comprising the cooperating generally parallel surface of the needle-holding retention body. Although the frictionally engaged surfaces of the retention body and movable member may be axially aligned in a longitudinal direction with respect to the tube member, they are preferably slightly tapered in such a way as to permit assembly of the two parts by applying a known force of desired magnitude which wedges the two parts into frictional engagement such that approximately the same force will be required to frictionally disengage them. A slight taper is provided which is wider at the back portion of the slidable interface and narrower at the front portion of the slidable interface so that the retraction body which holds the needle will be unwedged as the movable member moves axially forward while the retraction body is held stationary. This permits the biasing member or spring to rapidly and instantaneously drive the retraction body and needle into the retraction space in the movable member as the contact area at the slidable interface is reduced when the retraction force becomes greater than the frictional holding force, to cause retraction of the retraction body or needle member into the movable member or plunger, by parallel sliding of the cooperating generally parallel surfaces.

The movable member may be regarded as a hollow plunger having the retraction space, and the elongated tube member may be regarded as an elongated sheath body defined by a wall extending in the axial longitudinal direction. The sheath has an operating mechanism disposed within it. The operating mechanism comprises a hollow plunger body having a front portion mounted in sliding contact with the wall and a back portion extending from the sheath having an opening for insertion of a collecting tube. The front portion of the plunger has an opening having a surface for frictionally holding a needle holder. The needle holder has a cooperating surface which, together with the surface for frictionally holding the needle holder, comprise a sliding interface frictionally holding the needle holder within the opening. The operating mechanism further has a coaxial biasing means supported within the sheath in such a manner as to apply a biasing force to the needle holder upon axial movement of the plunger body.

A catch means is provided in the sheath body for holding the operating mechanism in an operating position. The operating position is a use position in which a needle connected to the needle holder is extended from the sheath body. The plunger is movable in the axial direction to a retraction position which is beyond the operating position, in sliding disengagement from the needle holder along the sliding interface until the needle holder slides free from the plunger. The needle holder is quickly retracted into a retraction space in the plunger in response to the biasing force and the needle holder and a needle connected thereto is retracted entirely within the sheath in response to movement of the plunger in an axial direction to a retraction position beyond the operating position. There is included means for preventing further movement of the needle holder in the axial direction when the plunger moves beyond the operating position, and thus the retraction is exactly controlled. Retraction is foolproof because when the plunger moves forward, the needle holder is restrained and sliding release must occur along the slidable interface. In order for retraction to occur, there is no need for flexing of parts, manual intervention, or breaking of parts.

The plunger body or movable member is preferably equipped with a positioning device which cooperates with a portion of the tube member or sheath to selectively position the plunger at the first or operating position and permit movement of the plunger to the second or retraction position to ensure retraction must occur. The positioning device is preferably a two-position cap carried by the plunger at the back portion thereof, which operates by engagement with the wall of the sheath. When the cap member is in a forward position with respect to the plunger, it bottoms out against the back end of the sheath to position the plunger in the first operating position. When the cap member is moved back to a second position farther back on the plunger, it then permits the plunger to be moved further forward from the first operating position to the second retraction position, thus ensuring retraction will occur.

The means for preventing the needle holder from moving beyond the first operating position may be provided by a nose portion of the retraction body which bottoms out against a stop surface positioned in the front end of the tube member. It is also within the contemplation of the invention that the forward movement prevention means could be provided by full compression of the biasing means to an incompressible state. This could occur by compressive stacking of the coils of a spring which effectively prevents further forward movement.

There is also provided a catch means which prevents withdrawal of the movable plunger from the sheath to prevent access to the needle after retraction has occurred. The coiled spring member has enough uncompressed length to ensure that the retracted needle is fully enclosed within the sheath after retraction occurs. Consequently, there is no danger of needle sticks after the device has been used, the collection tube removed and the plunger moved to cause retraction. The device preferably includes a detent in the wall of the tube member or sheath which may engage the outer facing portion of the head of the plunger to hold the device in a pre-use shipping position wherein the needle mounted in the needle holder is entirely enclosed until the plunger is moved forward slightly to release the detent.

Except for the canula needle and spring member, the device is preferably formed from plastic materials commonly used in syringe technology. The simple straight lines of the parts contribute to simplicity that makes the parts ideally suited for mass production of a practical, economical unit. No special molding technology is required to produce the parts in multiple out molds. There are no critical tolerances. A slightly tapered frictional engaging surface between the movable member and retractable body permit complete freedom of adjustment of the frictional holding force during assembly. This permits choice of the amount of retraction force that will be required to cause retraction in a completely reproducible manner.

BRIEF DESCRIPTION OF THE DRAWINGS

FIG. 3 is a device of FIG. 2 showing the cap member moved to the back or second position in preparation for retraction and including a capped evacuated collection tube which has been inserted through an opening in the movable member and punctured by the inner end of the canula needle;

FIG. 4 is a cutaway sectional view of the device of FIG. 3 after the collection tube has been removed and the plunger moved forward axially to cause retraction whereby the needle is fully enclosed within the sheath;

FIG. 5 is a perspective view of the plunger body of FIGS. 1-4;

FIG. 6 is a view on the lines 6—6 of the forward end of the movable plunger as shown in FIG. 5 with the addition of the retraction body or needle holder to show how it is coaxially positioned as in FIG. 1;

FIG. 7 shows the upper end of an alternative rear end of the plunger body showing a modified cap member which can be employed to provide a two-position plunger;

FIG. 8 is a cross-section of the modified plunger of FIG. 7 on the lines 8—8.

DETAILED DESCRIPTION OF THE INVENTION

Figure 1:
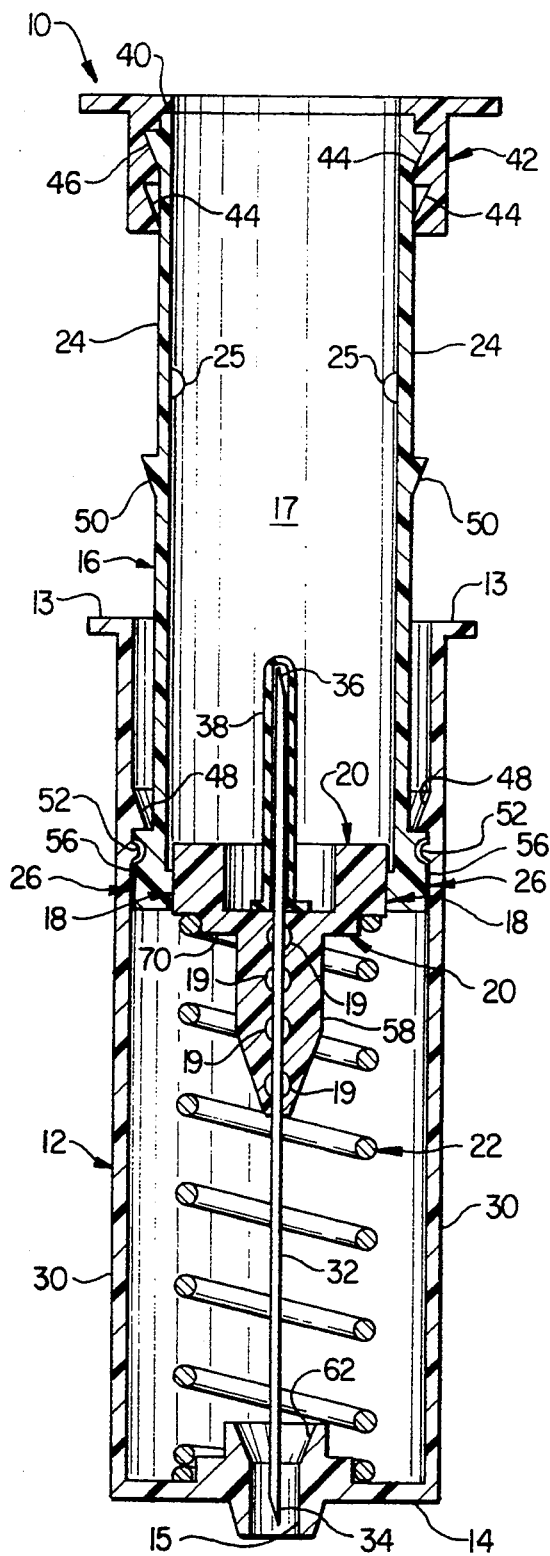
FIG. 1 is a diametrical cutaway view of the assembled retractable fluid collection device in the shipping position.

In FIG. 1, a fluid collection device is described generally by the reference numeral 10. Structure 10 has what may be referred to an elongated tube member or a sheath body 12. Tube member 12 has a front end portion 14 having a port 15.

Slidingly mounted within tube member 12 is a movable member or plunger 16 having a retraction space 17. Plunger 16 has a head portion 26 which is formed in an axially forward position of the plunger. Retraction body or needle holder 20 is frictionally held along slidable interface 18 within an opening of the front or head 26 of the plunger. Plunger 16 is coaxially mounted in tube member 12 in sliding contact with side wall 30 extending in an axial longitudinal direction. It is mounted for axial movement toward and away from front end 14.

A double-ended hollow canula needle 32 is fixedly mounted in retraction body or needle holder 20. Needle holder 20 may have a nose portion 58 having a series of axially aligned spaces 19 along an axial opening, which can accommodate an adhesive, such as epoxy, to secure needle 32. Needle 32 has a sharpened front end 34 and a sharpened rear end 36. A collapsible rubber sheath 38 covers the rear end portion of the needle to prevent contamination.

The rear end portion 40 of movable plunger 16 is equipped with a two-position cap member 42 which is schematically indicated in FIGS. 1-4. It is illustrated as having two sets of tapered gripping surfaces 44 which cooperate with a tapered gripping surface 46 near upper end 40 of movable plunger 16. A more sophisticated end cap is illustrated in FIG. 7 which will be described later.

Figure 2:
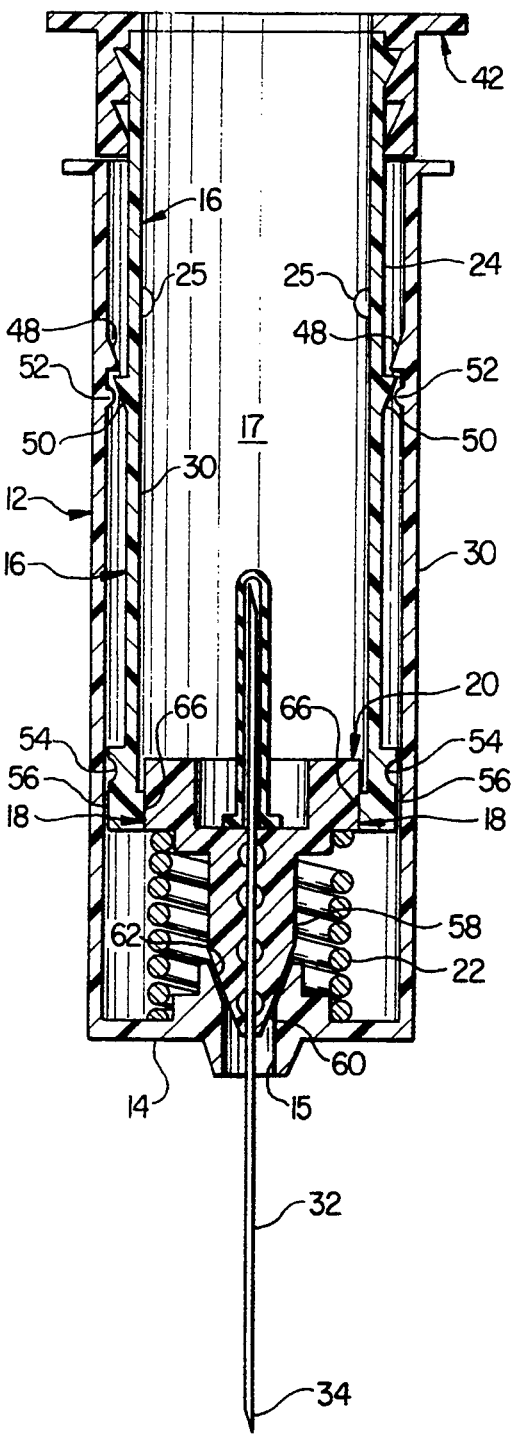
FIG. 2 is a diametrical cutaway view of the assembled retractable fluid collection device held in the first or operating position with one end of the canula extended for use.

By reference to FIG. 2, the longitudinally axially extending walls 24 and 30 have cooperating catch means 48 and 50. Wall 30 has an internally extending catch 48, whereas wall 24 has an outwardly extending catch 50 adapted to hold plunger 16 in the first position which is the operating position for use. Catches 48, 50 may be annular in nature. The inner surface of wall 30 may also be equipped with detents 52 adapted to cooperate with an annular groove 54 in head 26. Groove 54 is located in the outer peripheral surface 56 of head 26. In the shipping position of FIG. 1, detent 52 is shown engaged in groove 54, while a rear portion of head 26 is prevented from rearward axial movement by catch 48. These catches, detents and grooves are exaggerated for clarity. The plunger head is designed to slip forwardly over catch 48 to facilitate insertion from the rear end 13 of tube member 12.

Referring again to FIG. 2, needle holder 20 has a forwardly extending nose portion 58 having a tapered front portion 60 which, in the first position, bottoms out against stop surface 62 formed in front 14 of tube member 12. Nose portion 60 and stop 62 are tapered in such a way as to axially align the retraction body as the surfaces bottom out in contact with each other. Coaxial biasing member 22 could also comprise a stop for the needle holder by having the coils come into an incompressible state as the plunger is moved to the first position illustrated in FIG. 2.

By reference to FIG. 5, it is seen that head 26 may comprise a plurality of angularly spaced segments 64 which are evenly spaced around wall 24 and include inwardly extending arcuate lands 28 carrying cooperating generally parallel surfaces 66 best seen in FIG. 5. Cooperating generally parallel surfaces 68 are formed on the outer periphery of a portion of needle holder 20. This is another way to control the amount of frictional contact between the outer facing peripheral surfaces 68 of needle holder 20 and the inwardly facing peripheral surfaces 66 of head 26. Segments 64 can be smaller or larger or even fused into a complete ring which permits varying the amount of contact between the cooperating parallel surfaces 66, 68. Needle holder 20 may also have a circular flange 70 to fit the open upper end of spring 22.

FIG. 2 represents the first or operating position. Movable member 16 is selectively axially movable toward the front end of tube member 12 to a second position closer to the front end than the first position. It is readily seen that it will not take much movement of plunger 16 relative to tube member 12 in the axially forward direction to reduce the amount of frictional sliding engagement area 18 to a very small amount. If the plunger is moved an axial distance equal to the cooperating generally parallel surfaces 66 of head 26, it will be completely removed from contact with the needle holder which is under the influence of spring 22. Once it is moved the axial length of surfaces 66, retraction must occur because body 20 is under the biasing influence of a retraction force supplied by spring 22. In practice, the retraction will occur slightly before this full extent of movement is obtained when the retraction force exceeds the frictional holding force applied at sliding interface 18. Thus, the second position of plungers 16 is not precisely defined in terms of axial distance, except that it is axially forward of the first position an amount sufficient to allow the retraction to occur.

In FIG. 3, an evacuated collection tube 72 has a diaphragm or rubber cap 74. The rear end portion of end cap 42 has an opening 76 to receive tube 72. Movable member or plunger 16 similarly has an opening 78 at its rear end to receive tube 72. Plunger 16 is held in tube member 12 by catches 48,50 with canula needle 32 extended in the use position.

In operation, the device is assembled in the position of FIG. 1 to facilitate shipping without danger of damage to the needle or those handling the device. There is no need for a cover over the needle because the needle is fully enclosed within sheath 12. The detents lightly hold the plunger in the shipping position. In preparation for use, plunger 16 is depressed the full extent permitted by cap member 42 and catches 48,50 are engaged to hold the unit in the first operating position for use. Needle 32 is extended from the front of the sheath and needle holder 20 is bottomed out against the stop. Collection tube 72 is then inserted into openings 76,78 and brought into contact with rear end 36 of needle 32 without puncturing diaphragm 74. Cap member 42 is pulled back into the second position facilitated by the fact that plunger 16 is held by catch 48 in sheath 12.

Now when the sharpened end 34 of needle 32 is inserted into a patient in fluid communication with the vein, tube member 72 is pushed forward, causing sharpened end 36 to puncture diaphragm 74 and allow the blood to be collected into evacuated chamber 80 in tube 72. When a sufficient sample has been collected, the device is removed from the patient and collection tube 72 withdrawn from the device. It then looks like FIG. 2, except that the cap member has been pulled backwardly to the second position shown in FIG. 3. The plunger is then pushed forward toward the second position, causing a reduction of the area or extent of the sliding interface 18, as plunger 16 moves relative to needle holder 20. Needle holder 20 is fixed and cannot move. When the plunger moves forward to the point where the retraction force provided against needle holder 20 by spring 22 exceeds the frictional holding force at sliding interface 18, the needle holder is retracted into retraction space 17. Retraction occurs quickly and the retracted position is that shown in FIG. 4. Spring 22 extends to its full uncompressed height to drive needle holder 20 into the retraction space in plunger 16. Needle 32, including sharpened end 34, is completely withdrawn through port 15 in front 14 into sheath 12. Retraction is quick and permanent. There is no way to re-extend the needle once the needle holder has been frictionally disengaged from plunger 16. The inner surface of plunger 16 may include one or more stops 25 which prevent needle holder 20 from being ejected or removed through the back of plunger 16. These are exaggerated and designed to allow insertion and removal of collection tube 72 while retaining the retracted needle holder inside the device as shown in FIG. 4.

An alternative two position end cap 82 is shown in FIGS. 7 and 8. End cap 82 has a thumb ring 84 with an opening 86 for the collection tube and a depending wall 88 having protrusions 90 on the inside surface. The upper end of plunger 16 is modified to include one or more channels 92 formed in the outer side wall 24. Channels 92 are "J" shaped and include one way stops 94 which allow protrusions 90 to move in one direction when they are inserted in channels 92. This provides a two position end cap, a front position when protrusions 90 are between the two stops and a rear position when they are pulled back over the second stop 94. The cross section of FIG. 8 shows the position of stops 94 in channels 92. The stops are exaggerated for clarity.

The device is easily assembled for mass production. Needle 32 is epoxied into needle holder 20. Rubber sheath 38 may be placed over end 36 of the needle and fastened to the needle holder by adhesive. This assembly is inserted through the rear opening of the plunger. Cooperating surfaces 66 of the plunger and 68 of the needle holder are axially oriented generally parallel to the needle to comprise slidable interface 18. They are preferably tapered slightly toward the front so that needle holder 20 can be easily started into the opening in head 26 from the rear and wedged into frictional engagement under a predetermined and consistent load. If, for example, they are wedged under a load of two pounds, then they can be unwedged by approximately the same two pounds when the plunger is pushed forward to cause retraction. If a greater force is desired, a greater load can be applied during assembly. This makes assembly well suited to automation and greatly enhances reproducibility since the same assembly force can be applied to each unit. This also has the advantage that manufacturing tolerances are less critical. If the outer periphery of the needle holder is slightly less, it will simply move forward slightly until the desired frictional engagement is obtained. It is desirable to mold the needle holder and plunger from the same plastic material to minimize any differential in thermal expansion in case the retractable device is exposed to variations in ambient temperatures.

The parts are preferably circularly shaped, although it is within the contemplation of the invention that non-circular cross sectioned parts could be employed. The slidable interface could have a non-circular shape if the opening in the plunger was not round and the needle holder had a corresponding non-round periphery. It is also within the contemplation of the invention that the plunger could have a single position end cap instead of a two position end cap provided the end cap were placed equivalent to the rearmost portion so that it would not interfere with retraction. Movement of the plunger would be stopped when the user feels the plunger lock into the first position. Then after use, the plunger could be pushed further forward to cause retraction without interference from the end cap. If the walls of the device are clear, it is easy to see where the plunger is and also verify that retraction has occurred. Other obvious variations may be made to the preferred embodiment without departing from the spirit of the invention or the scope of the claims.

I claim:

1. A retractable fluid collection device for use in collecting fluid from a subject, comprising:

an elongated tube member having a longitudinal axis and a front end;

a movable member having a retraction space, said movable member mounted within said tube member for movement along the longitudinal axis toward the front end of the tube member;

a retraction body frictionally held by said movable member along a generally longitudinally oriented slidable interface comprising at least one cooperating generally parallel surface on the retraction body and at least one cooperating generally parallel surface on the movable member;

the movable member together with the frictionally held retraction body being movable along said longitudinal axis toward the front end of the tube member to a first position, and the movable member being movable to a second position closer to said front end than said first position;

a biasing means mounted in the front end of the tube member to push against the retraction body with a retraction force;

retraction force applied to the retraction body by said biasing means, tending to cause retraction of said retraction body into said retraction space; and retraction occurring by sliding release of said retraction body relative to said movable member along said slidable interface in response to said retraction force when said movable member is moved axially in the longitudinal direction, relative to said elongated tube member and said retraction body, from said first position to said second position.

2. The retractable fluid collection device of claim 1 wherein the movable member has a forwardly positioned head having one or more inwardly facing lands comprising said at least one cooperating generally parallel surface of said movable member which frictionally engage said at least one cooperating generally parallel surface of said retraction body to form said slidable interface.

3. The retractable fluid collection device of claim 2 wherein the at least one cooperating generally parallel surface of said retraction body comprise an outwardly facing peripheral surface of a portion of said retraction body.

4. The retractable fluid collection device of claim 3 wherein said retraction body has a circularly shaped outer peripheral surface comprising said at least one cooperating generally parallel surface.

5. The retractable fluid collection device of claim 1 wherein the elongated tube member is constructed with a means for preventing forward movement of the retraction body during movement of the movable member between the first and second position.

6. The retractable fluid collection device of claim 5 wherein said means for preventing forward movement of the retraction body includes a nose portion of the retraction body which bottoms out against a stop surface positioned in the front end of said tube member.

7. The retractable fluid collection device of claim 6 wherein said nose portion and said stop surface are tapered in such a way as to axially align the retraction body as they come into contact.

8. The retractable fluid collection device of claim 6 wherein the retraction body includes a needle extending from said nose portion of the retraction body, said needle being extended for use from the front end of the tube member when said movable member is in the first position, said needle member being withdrawn into said tube member when retraction occurs upon movement of said movable member to said second position.

9. The retractable fluid collection device of claim 8 wherein a catch means positions the movable member together with the frictionally held retraction body in the first position.

10. The retractable fluid collection device of claim 9 wherein said needle extends through the retraction body into said retraction space, said retraction space being sized to receive a collecting tube in fluid communication with said needle for delivery of fluid from a subject when said movable member is in said first position.

11. The retractable fluid collection device of claim 5 wherein said biasing means is adapted to be compressible by movement of the movable member and retraction body to said first position and incompressible upon further movement of said movable member between said first and second position so that said incompressible biasing means serves as the means for preventing forward movement of the retraction body during movement of the movable member between said first and second position.

12. The retractable fluid collection device of claim 11 wherein the biasing means is a coil spring sized to reach an incompressible state by interference of the coils when the movable member is moved to the first position.

13. The retractable fluid collection device of claim 5 wherein said movable member is equipped with a two-position cap which cooperates with a portion of said elongated tube member to selectively position said movable member at said first position and permit movement of said movable member to said second position.

14. The retractable fluid collection device of claim 13 wherein a catch means positions the movable member together with the frictionally held retraction body in the first position.

15. The retractable fluid collection device of claim 14 wherein said elongated tube member has a side wall and said catch means is positioned on the inside of said side wall to cooperate with a complimentary catch on the movable member.

16. A retractable fluid collection device for use with a fluid collection tube for collecting fluid from a subject, comprising:

an elongated sheath body defined by a wall extending in an axial longitudinal direction;

an operating mechanism disposed within the sheath, the operating mechanism comprising:

a plunger having a hollow body with a front portion mounted within said wall and a back portion extending from the sheath body, the plunger back portion having an opening for insertion of a collecting tube;

the front portion of the plunger having an opening therein having a surface for frictionally holding a needle holder;

a needle holder having a cooperating surface comprising with said surface a sliding interface frictionally holding said needle holder within said opening, the needle holder being movable with said plunger against a biasing force;

a coaxial biasing means supported within the sheath in such a manner as to apply said biasing force to the needle holder upon axial longitudinal movement of the plunger body;

catch for selectively holding the operating mechanism in an operating position; and the plunger being movable in said axial longitudinal direction to a retraction position, beyond the operating position, causing sliding disengagement of the plunger from the needle holder along said sliding interface until the needle holder slides free from the plunger, whereupon the needle holder is retracted into the plunger in response to the biasing force applied against the needle holder by said biasing means;

whereby the needle holder is entirely retracted within the sheath in response to movement of the plunger in an axial longitudinal direction to a retraction position beyond the operating position.

17. The retractable fluid collection device of claim 16 further including means for preventing further movement of the needle holder in the axial longitudinal direction when the plunger moves beyond the operating position.

18. The retractable fluid collection device of claim 17 wherein said sliding interface is generally oriented in the axial longitudinal direction of movement, said sliding interface having an area of sliding contact being gradually reduced as said plunger moves beyond the operating position toward the retraction position in sliding disengagement from the needle holder until the frictional holding force between the plunger and the needle holder is reduced to less than the biasing force applied against the needle holder by the biasing means.

19. The retractable fluid collection device of claim 16 wherein said plunger is equipped with a positioning device which cooperates with a portion of said elongated sheath body to selectively position said plunger at the operating position and permit movement of the plunger to the retraction position to ensure retraction must occur.

20. The retractable fluid collection device of claim 19 wherein said positioning device is a two-position cap member carried by the plunger at the back portion thereof which operates by engagement with the wall of the sheath.

21. A retractable fluid collection device for use with a collection tube, comprising:

an elongated hollow sheath defined by a side wall extended in a longitudinal axial direction to a front end of the sheath;

a plunger having a hollow body defined by a side wall, the plunger body being extended in a longitudinal axial direction between a rear portion having an opening for a collection tube and a front portion having a front opening therein, said plunger being mounted within the side wall of the sheath for axial movement toward and away from the front end of said sheath;

a needle holder frictionally held for movement with the plunger by means of a slidable interface formed by cooperating surfaces of the needle holder and the front opening of the plunger;

said slidable interface being generally oriented in a longitudinal axial direction and providing a sliding frictional engagement force to hold the needle holder within the front opening of the plunger in opposition to a biasing force applied to the needle holder;

a spring mounted in the sheath to apply said biasing force to said needle holder;

a needle mounted to extend from the needle holder;

the plunger being longitudinally axially moveable to position the needle holder at the front of the sheath at a use position with the needle extended from said sheath, wherein the frictional engagement force exceeds the biasing force; and the plunger being longitudinally axially movable toward the front of the sheath to a release position wherein said biasing force overcomes said frictional engagement force in response to sliding reduction of the extent of the sliding interface whereby the needle holder is retracted into said hollow body of the plunger a sufficient distance to withdraw the needle within said sheath.

22. The retractable fluid collection device of claim 21 wherein catch means is provided to secure the plunger in said use position and prevent said plunger from being withdrawn from said sheath.

23. The retractable fluid collection device of claim 22 wherein the plunger is provided with stop means positioned on the sidewall at a longitudinal axial location which allows the needle holder to be retracted by the spring a sufficient distance to retract the needle within the sheath and serves to retain the needle holder in the plunger.

24. The retractable fluid collection device of claim 23 wherein the needle holder has a forwardly extending nose portion which cooperates with a stop means located at the front end of the sheath to stop the needle holder from moving forward beyond the use position while the plunger is moved forwardly toward the release position.

25. The retractable fluid collection device of claim 24 wherein the plunger has a two-position end cap which has a first position which prevents the plunger from moving between the use position and the release position and a second position which allows the plunger to move forward to the release position.

26. A retractable fluid collection device for use with a collection tube, comprising:

an elongated tube member having a closed front end portion equipped with a port through which a needle may be extended;

a hollow plunger slidably mounted within said tube for selected movement toward and away from the front of said tube member, said plunger having a front end portion formed with an opening therein;

the opening in the front end portion of the plunger having a holding surface defining the perimeter of said opening;

a retractable needle holder having an outer perimeter surface formed to correspond to the shape and orientation of the perimeter of said opening at a slidable interface, the needle holder being slidably frictionally engaged with the plunger at said interface and being disengageable therefrom upon application of a friction force to said needle holder;

a biasing member arranged in the tube member to apply an increasing retraction force to said needle holder during movement of said plunger forwardly toward the front end portion of the tube;

the plunger and retractable needle holder being movable forwardly together against said retraction force to a first position wherein said friction force exceeds said retraction force and the needle holder remains held unretracted;

means for holding said needle holder in said first position;

the plunger being movable forwardly toward a second position beyond said first position whereupon the retraction force overcomes said friction force to cause sliding separation of the needle holder by parallel sliding along said slidable interface whereby said friction force is reduced and the needle holder is suddenly retracted into the hollow plunger.

27. The retractable fluid collection device of claim 26 wherein the plunger has a rear end portion equipped to receive a collection tube therein and a needle which extends frontwardly and rearwardly from said needle holder.

28. The retractable fluid collection device of claim 27 further including a collection tube with a seal that can be punctured by the needle extending rearwardly from the needle holder in fluid communication through the remainder of the needle with a subject when the plunger is in said first position.

* * * * *